(12) United States Patent
Prevost et al.

(10) Patent No.: US 8,093,023 B1
(45) Date of Patent: Jan. 10, 2012

(54) DE-FATTED SOY PRODUCTION PROCESS AND VALUE ADDED BY-PRODUCTS FROM DE-FATTED SOY FLOUR

(75) Inventors: John E. Prevost, Slaughter, LA (US); Neal A. Hammond, Cameron Park, CA (US)

(73) Assignee: Little Sioux Corn Processor, LLC., Marcus, IA (US)

( * ) Notice: Subject to any disclaimer, the term of this patent is extended or adjusted under 35 U.S.C. 154(b) by 1705 days.

(21) Appl. No.: 11/162,945

(22) Filed: Sep. 28, 2005

Related U.S. Application Data

(63) Continuation-in-part of application No. 10/458,480, filed on Jun. 10, 2003, now Pat. No. 7,300,680, which is a continuation of application No. 10/008,834, filed on Nov. 9, 2001, now abandoned, which is a continuation of application No. 09/229,286, filed on Jan. 13, 1999, now abandoned, application No. 11/162,945, which is a continuation-in-part of application No. 10/710,125, filed on Jun. 21, 2004, now abandoned, which is a continuation-in-part of application No. 10/708,326, filed on Feb. 24, 2004, now abandoned, which is a continuation-in-part of application No. 10/619,833, filed on Jul. 15, 2003, now abandoned, which is a continuation-in-part of application No. 10/395,547, filed on Mar. 24, 2003, now abandoned, which is a continuation-in-part of application No. 10/281,490, filed on Oct. 28, 2002.

(51) Int. Cl.
*C12P 7/06* (2006.01)

(52) U.S. Cl. ......... 435/161; 435/41; 435/68.1; 435/163; 435/165; 435/195; 435/201

(58) Field of Classification Search ............... 435/41, 435/68.1, 161, 163, 165, 195, 201
See application file for complete search history.

(56) References Cited

U.S. PATENT DOCUMENTS

| 4,286,058 | A  | * | 8/1981  | Wenger et al. | 435/99  |
|-----------|----|---|---------|---------------|---------|
| 4,361,651 | A  | * | 11/1982 | Keim          | 435/161 |
| 4,447,535 | A  | * | 5/1984  | Zucker et al. | 435/162 |
| 5,231,017 | A  | * | 7/1993  | Lantero et al.| 435/161 |
| 6,569,653 | B1 | * | 5/2003  | Alard et al.  | 435/161 |
| 2002/0004095 | A1 | * | 1/2002 | Whalen      | 426/598 |
| 2003/0104587 | A1 | * | 6/2003 | Verser et al. | 435/135 |
| 2004/0234649 | A1 | * | 11/2004 | Lewis et al.  | 426/31  |

* cited by examiner

*Primary Examiner* — Allison Ford
*Assistant Examiner* — Susan E Fernandez
(74) *Attorney, Agent, or Firm* — Camille L. Urban

(57) ABSTRACT

An improved process for producing de-fatted soy utilizing a de-fatted soy flour and for producing value added by-products from de-fatted soy flour wherein soybeans are de-hulled and the de-hulled stream ground to a flour consistency. The ground soy flour is mixed with water and other additives to produce a vitamin and mineral enriched stream that is then filtered to various value added by-products. In a preferred embodiment the vitamin and mineral enriched stream is filtered through a 0.1-1.0 micron membrane to produce a de-fatted soy product stream and a fatted soy product stream. The fatted soy product stream can be dried to produce dry, less than 12% water by weight, product for use in cosmetics and pharmaceutical products. The de-fatted soy product can be filtered through reverse osmosis (RO) filtration unit to obtain a vitamin and mineral enriched product stream that can be dried to powder form and used as a food supplement additive. If desired the full fatted soy flour or the de-fatted soy product stream can be combined with whole stillage from an ethanol process and used in producing various other value added products.

20 Claims, 4 Drawing Sheets

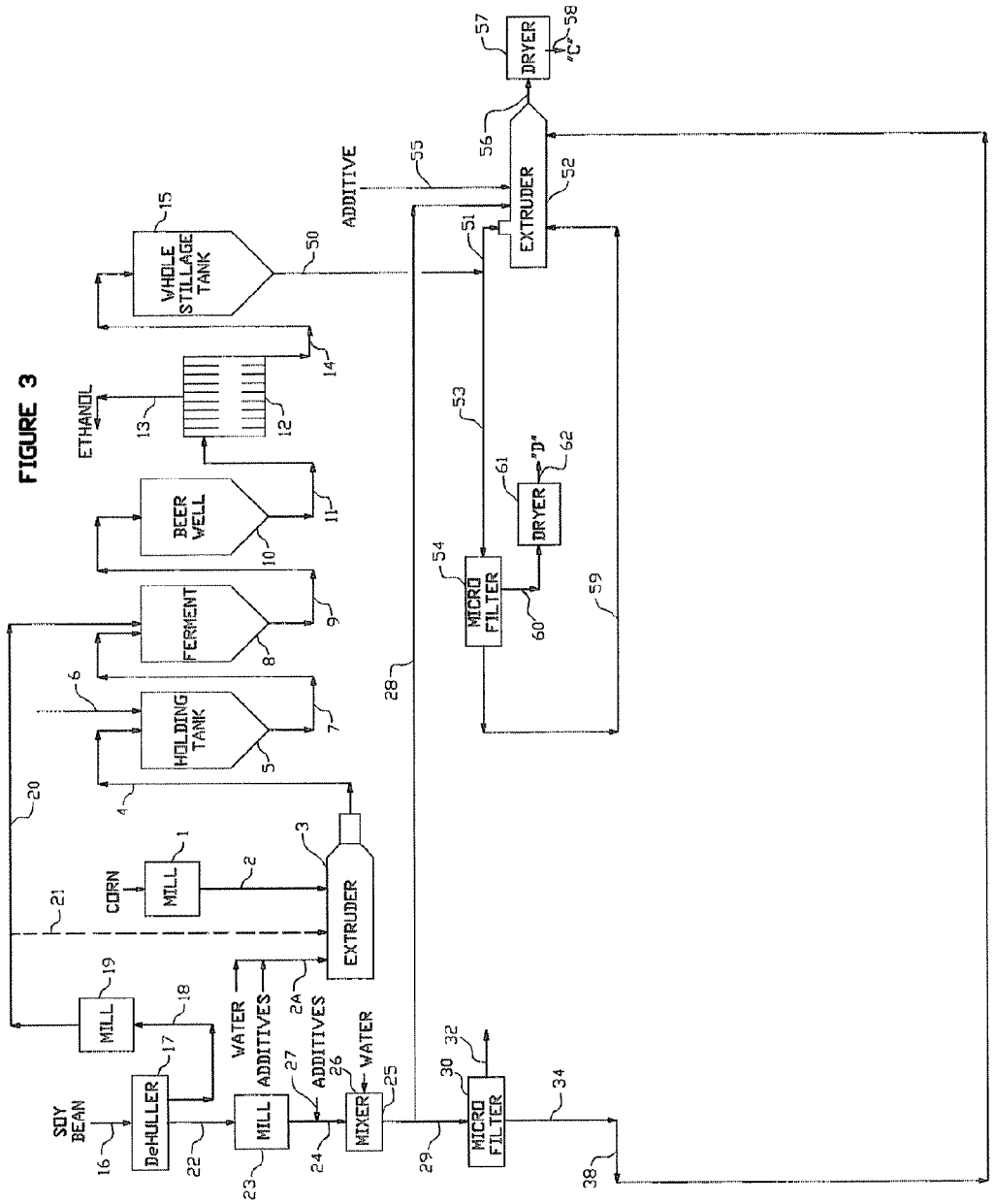

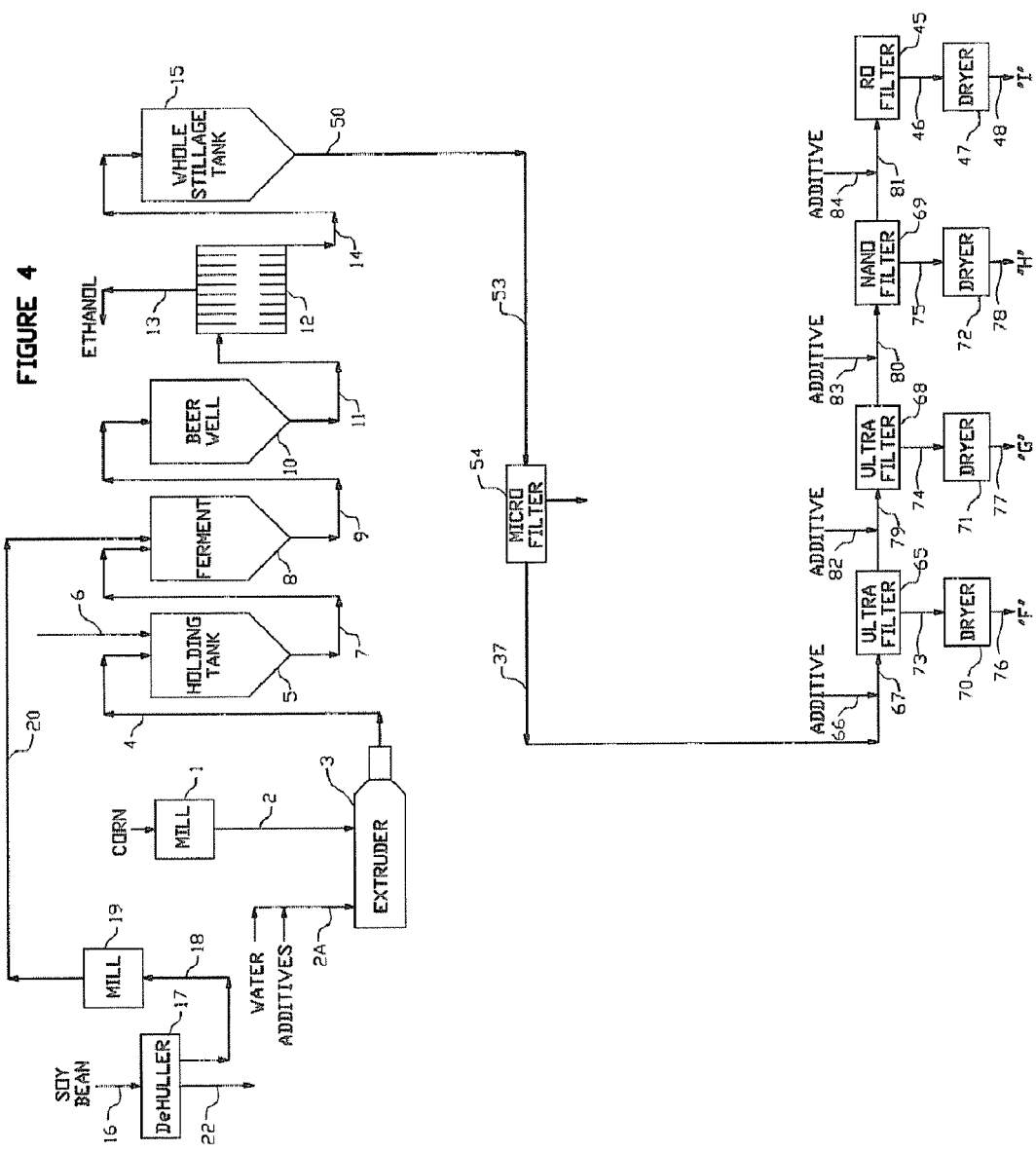

DE-FATTED SOY PRODUCTION PROCESS AND VALUE ADDED BY-PRODUCTS FROM DE-FATTED SOY FLOUR

CROSS-REFERENCE TO RELATED APPLICATIONS

This application is a continuation-in-part of U.S. patent application Ser. No. 10/458,480 filed Jun. 10, 2003 now U.S. Pat. No. 7,300,680, which in turn is a continuation of U.S. patent application Ser. No. 10/008,834 filed Nov. 9, 2001 now abandoned, which in turn is a continuation of U.S. patent application Ser. No. 09/229,286 filed on Jan. 13, 1999 now abandoned.

This application is also a continuation-in-part of U.S. patent application Ser. No. 10/710,125 filed Jun. 21, 2004 now abandoned, which is a continuation-in-part of U.S. patent application Ser. No. 10/708,326 filed Feb. 24, 2004 now abandoned, which is a continuation-in-part of U.S. patent application Ser. No. 10/619,833 filed Jul. 15, 2003 now abandoned, which is a continuation-in-part of U.S. patent application Ser. No. 10/395,547 filed Mar. 24, 2003 now abandoned, which is a continuation-in-part of U.S. patent application Ser. No. 10/281,490 filed Oct. 28, 2002.

BACKGROUND OF THE INVENTION

1. Field of the Invention

This invention relates in general to an ethanol production process, and more particularly to methods of producing ethanol and whole stillage from a carbohydrate containing feedstock, such as corn, with and without a soy based feedstock, such as soybeans, and subsequent treatments of the whole stillage to produce recoverable value-added products.

2. Prior Art

With the ever-increasing depletion of economically recoverable petroleum reserves, as well as the environmental impact of the drilling processes to effect the recovery, the production of ethanol from carbohydrate containing sources as a partial or complete replacement for conventional fossil-based liquid fuels has become more attractive. A variety of materials have been utilized as the starch or sugar-containing feedstock in ethanol producing processes. One of the most common feedstock is whole corn kernels. In a conventional ethanol production process utilizing corn as the initial feedstock, the corn is first ground to produce a milled corn. This is typically achieved by the use of a hammer mill or other similar conventional milling equipment. Water, nutrients, and enzymes are then added to the milled corn to form a liquefied slurry. The liquefied slurry is then mixed in a fermentation vessel with water, yeast, and selected minerals and nutrients, whereby it then undergoes fermentation. The fermented product, commonly referred to as the "beer" is then distilled to produce an ethanol rich stream (about 95% ethanol and 5% water by weight) and a whole stillage, comprising water, as well as the solids resulting from the fermentation, from which by-products are then recoverable. Unfortunately, the by-products obtained from the conventional ethanol producing processes do not have sufficient economic value because of their relative low nutrient content to permit these processes from economically competing with conventional fossil fuel processes. Furthermore, because of the economics involved in the current process, the costs of producing ethanol and other resultant by-products has remained relatively high when compared to the fossil fuel sources, and such ethanol production processes have remained economically viable due mostly to government subsidies. Efforts to improve the economic viability of these processes have been addressed, but there still remains demand for the gain of further economic benefit from the use of an ethanol production process. Further improvements to the ethanol producing process that can either achieve processing cost savings or enhanced value by-products are therefore desirable.

OBJECTS AND SUMMARY OF THE INVENTION

It is an object of the invention to provide an improved ethanol and whole stillage production process that provides processing cost savings.

It is an another object of this invention to provide an improved whole stillage treatment process that results in the production and recovery of value-added products, including nutritional, nutraceutical, flavor enhancing, cosmetic, and/or pharmaceutical products.

It is still another object of this invention to provide a process for treatment of soybeans to produce an improved feedstock for use in an ethanol process, as well as to produce value-added products from the soybeans.

These and other objects and advantages of the invention shall become apparent from the ensuing figures and descriptions of the invention.

Accordingly, an improved process for producing ethanol and whole stillage is disclosed. The carbohydrate containing feedstock, such as whole corn kernels, is first subjected to a milling process to achieve a predetermined and preferred granulation that allows for a more efficient treatment by the subsequent hydrolysis and fermentation steps. In a preferred embodiment the feedstock will be milled to a flour consistency; i.e., having a median particle size of less than about 100 microns. Water and additives, such as nutrients and pre-determined enzymes, are then added to the milled feedstock in a predetermined and preferred ratio to form liquefied slurry. The slurry is then extruded under preferred time, pressure, and temperature conditions that promote the hydrolysis of the corn. The hydrolysis can be performed utilizing any number of known mixing apparatus that can control temperature and pressure of its contents. For example this could include a steam-jacketed pressure mixer operating under pressure. It could also include a steam-jacketed extruder. Particular extruders include a twin screw type extruder, that results in both mixing and hydrolysis of the slurry. The extruded slurry is subsequently subjected to fermentation and then distillation processes carried out under known fermentation and distillation conditions to produce an ethanol rich stream and a whole stillage. In a preferred embodiment the whole stillage will be treated by various filtration steps to recover value-added by-products. In another preferred embodiment, soy materials resulting from the processing of soybeans are added to various phases of the ethanol and whole stillage production and by-product recovery process.

The milling, extrusion, fermentation, and whole stillage treatment methods provided for by the present invention, in conjunction with the utilization of soy additives, result in an overall improved ethanol and by-product production process that achieves processing cost savings and recovery of value-added by-products useful as nutrient supplements for food products, or in the formulation of cosmetic products, and/or neutraceutical products, and/or pharmaceutical products.

BRIEF DESCRIPTION OF THE FIGURES

The accompanying drawings illustrate several preferred embodiments of the invention. However, it is to be understood that these embodiments are not intended to be either exhaustive, or limiting of the invention. They are but examples of some of the forms in which the invention may be practiced.

FIG. 3 is a schematic flow chart illustrating a preferred embodiment of the process utilizing the whole stillage produced by the preferred ethanol process to produce a protein rich nutrition product useful as a food supplement, as well as an oil-protein-carbohydrate rich emulsion product.

FIG. 4 is a schematic flow chart illustrating a preferred embodiment of the process of producing from the whole stillage various value-added products, such as a non-zein corn enriched product, a zein protein enriched product, a cyclodextrin enriched product, and a vitamin, mineral, carbohydrate small molecule enriched product.

DETAILED DESCRIPTION OF THE INVENTION

Without any intent to limit the scope of this invention, reference is made to the Figures in describing the preferred embodiments of the invention.

Although the preferred embodiments of this invention are described utilizing a whole kernel corn feedstock, it is understood that this process can also be carried out utilizing a variety of other carbohydrate-containing materials, such as molasses, bagasse, sugar beets, artichokes, and cereal grains such as barley and wheat. It is also to be understood that alternative protein-containing materials resulting from the processing of other protein-containing feedstocks, such as whey, can be used as additives to the various stages of the process.

Figure 1:
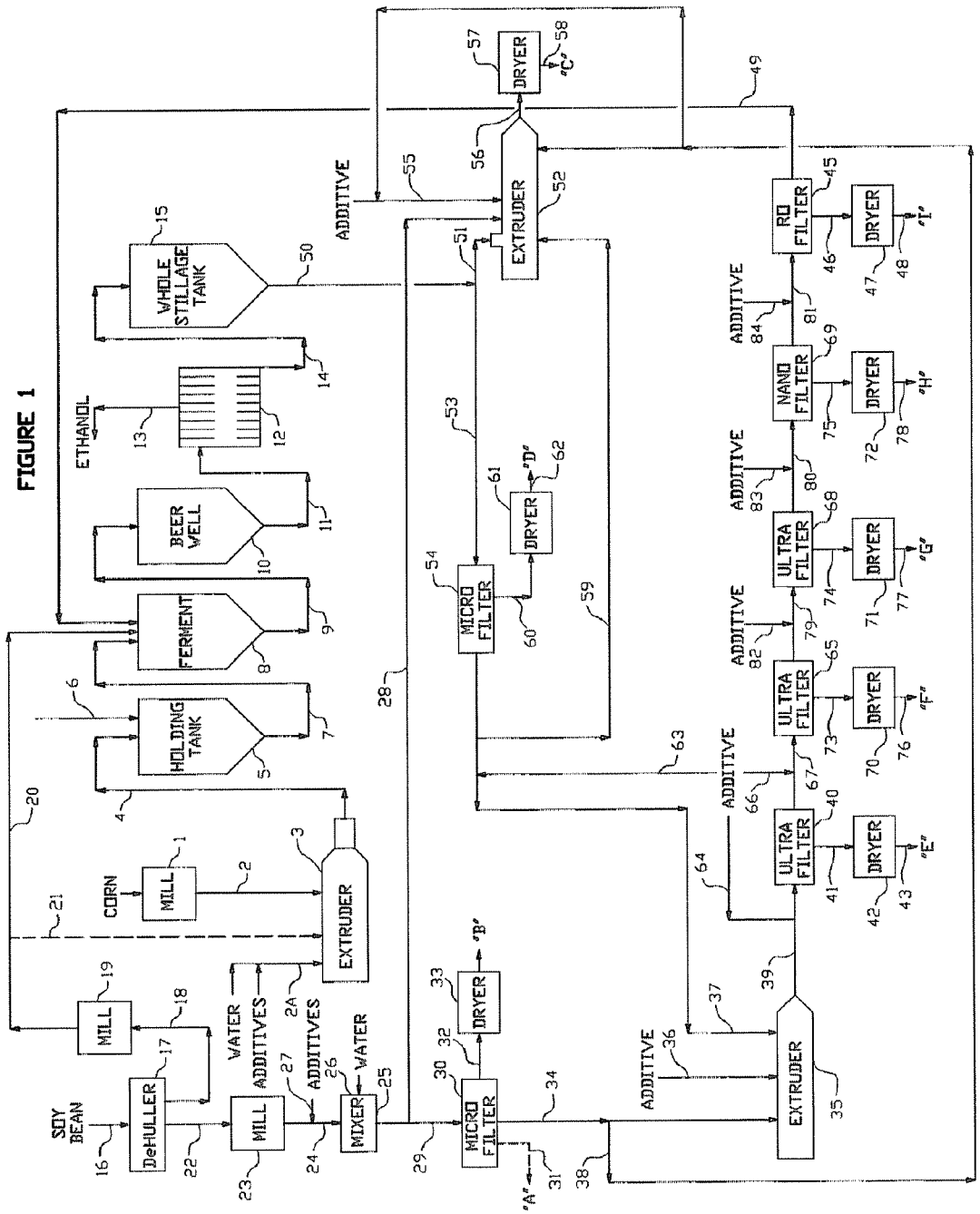
FIG. 1 is a schematic flow chart illustrating an integrated process utilizing both soybean and whole kernel corn feedstocks to produce ethanol and various value-added by-products from the whole stillage and the soybeans.
Figure 2:
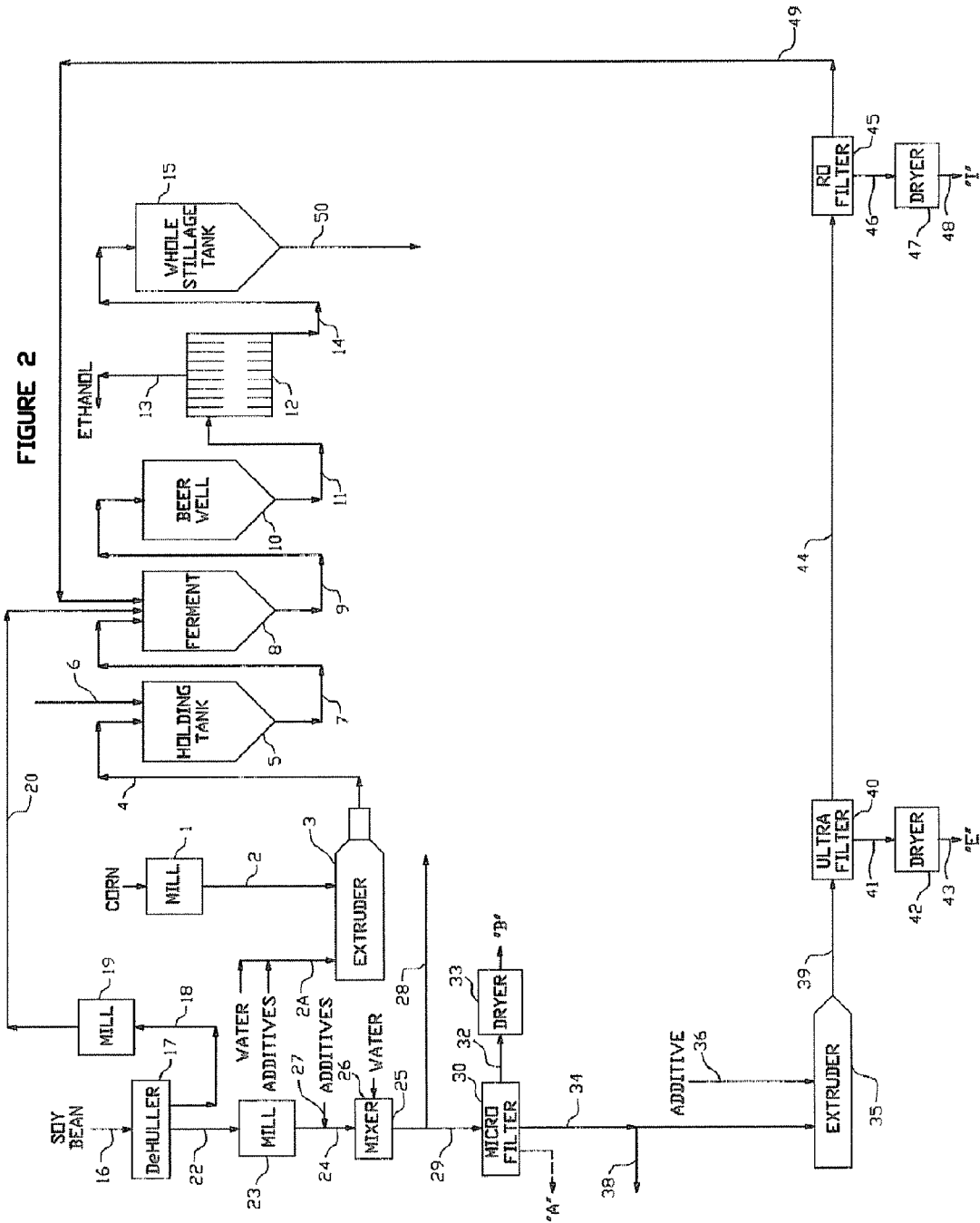
FIG. 2 is a schematic flow chart illustrating a preferred embodiment of the ethanol and whole stillage production process of the present invention utilizing both a soybean and a whole corn kernal feedstock and the production value-added by-products from the soybean feedstock.

Referring now to FIGS. 1 and 2 an integrated soybean and whole corn kernel feedstock process is illustrated that produces ethanol and whole stillage having improved value, as well as, various value-added by-products from the soybeans. In the preferred process whole kernel corn are first cleaned in a washing apparatus in preparation for milling. The washed corn is then feed to mill 1 to reduce the particles size of the kernels and break any outer protective covering, such as the pericap, to expose the inner starch and protein components of the kernel. More preferably the corn will be ground to a flour consistency; i.e., having a median particle size of less than about 100 microns. This novel step results in greater ethanol production efficiency, as well as improves the later filtration treatment of the whole stillage to produce the various value-added by-products possible with this invention. This is a departure from traditional ethanol production process where the corn is ground to a meal consistency in order to allow easier separation of the animal feed by-product in the whole stillage.

The flour will be combined in extruder 2 with water and additives from line 2A to form a slurry. Additives that can form part of the slurry in extruder 3 include enzymes, such as 1% alpha-amylase. Other amylase enzyme types, as well as other enzymes can also be utilized to advantage, depending on the desired by-products to be obtained from the subsequent treatment of the whole stillage. In another novel feature the amount of enzymes added is set at about 0.5% to about 1.5% by dry weight rather than the traditional 0.1% by dry weight. In another aspect of this invention multiple enzymes can be simultaneously used. In this embodiment the enzymes are selected to enable each to perform its function in the same processing environment without interference in the later production of ethanol during the fermentation step. The additives can also include selected nutrients, such as mineral containing compounds, as well as nitrogen containing compounds, such as phosphorus, calcium, and potassium. Preferably the selected nutrients should enhance the rate and efficiency of the subsequent fermentation phase. The amount of water, enzymes and nutrients in the slurry can be varied from about 70% to about 90% by weight of the corn flour. Preferably, the corn flour, water, enzymes, and nutrients are mixed in a ratio of about 100:20:1.5:1 to about 100:15:0.5:0.5 by weight to form the slurry.

The slurry is then mixed and hydrolyzed. Known equipment can be used to achieve these steps. One such equipment is extruder 3 chosen to perform not only the mixing of the corn, water, and additives, but to also perform the hydrolysis of the resulting slurry. Known extruders that can perform this dual task include many commercially available twin screw extruders, such as the Wenger TX-52, the Baker Perkins MPC/V 80, the APV SB80, the Werner & Pfleiderer ZSK-92, the Clextral BC 92, and the Buhler BVTF-93, as well as certain single screw extruders, such as the Anderson 4" extruder.

To promote the hydrolysis of the slurry, the operating conditions of extruder 3 are set to optimize conversions of the starches in the slurry to dextrins. In a preferred embodiment the slurry is subjected to the cooking in extruder 3 for a period of time and under temperature and pressure conditions that result in hydrolytic reactions that partially gelatinize corn flour and cleave the terminal amylose groups of the corn starch molecules. Since the temperature, pressure, and reaction time variables are interrelated, a higher pressure will result in a higher temperature, which in turn, will increase the reaction rate and result in more cleavage. In a preferred embodiment the slurry is extruded under conditions sufficient to cleave at least 20%-40% of the terminal amylase groups from the corn starch molecules, with as many as economically feasible preferably being cleaved. In general, extrusion cooking utilizes the extruder motor driven rotating screws to force a relatively dry mass (e.g., 10%-40% moisture) down the extruder barrel having a plurality of zones with holding tubes situated therebetween. A shaping die located at the outlet of the barrel causes the mass to pressurize and its temperature to rise. The pressure generated can rise to 300-3000 psi, causing the internal temperature to rise above the normal boiling point of water, without the production of steam or loss of moisture. Under such conditions, a cereal-based food mass will heat to 100° C. to 200° C. in less than two seconds and undergo hydrolytic reactions and convert to a homogenous gelatinized mass. In a conventional ethanol production process the hydrolysis is conducted at ambient pressure and at about 105° C. The slurry is maintained under these conditions for about 15 minutes to complete the hydrolysis. However, in this invention it is preferred that the slurry is extruded at moderate pressure (e.g., about 500 psi) for 45-60 seconds, with the temperature conditions ranging from 80° C. to 130° C. Under these conditions and with the use of additional enzymes this phase of the process functions as a catalyst to encourage a faster rate of corn starch hydrolysis and terminal amylase residue production. These terminal amylase residues, in turn, serve a critical function, as they appear to be responsible for the principle fermentation improvement properties of the corn flour hydrolysates, products of corn flour hydrolysis that serve as a fermentation media. This permits a more efficient treatment by the subsequent fermentation step. Browning of the mass can be reduced or eliminated by cooling the ends of the extruder 3 by known methods and apparatus. Necessary pH adjustments to the mass may be made by transferring the mass through line 4 to a holding tank 5 where pH adjustment streams can be added by line 6 and mixed with the homogenous gelatinized mass in tank 5.

The extruded slurry from holding tank 5 is then fed via line 7 to fermentation tank 8 where it undergoes fermentation. Because the ethanol and whole stillage production process of this invention utilizes a finer corn flour product, and further includes an extrusion-cooking phase promoting the hydrolysis of the finer corn flour, the rate of fermentation is more rapid, and the amount of ethanol recovered from the distillation step is greater. As also discussed below, the fermentation rate can further be improved with the addition of soy hull flour to the slurry in fermentation tank 8. Accordingly, the invention provides for a faster and more efficient ethanol and whole stillage production, which in turn, achieves processing cost savings and improves the overall economic viability of the ethanol and whole stillage production process.

After the slurry has undergone fermentation 26, the fermented slurry (aka/liquor or beer) is sent via line 9 to the beer well 10. From beer well 10 the fermented slurry is transported via line 11 to distillation column 12 where under heat and vacuum evaporated ethanol is recovered via line 13. The remaining water containing liquid after ethanol removal is called whole stillage and can be recovered from distillation column 12 via line 14. The whole stillage comprises components native to the corn plant that remained unchanged during the fermentation phase. In addition it comprises components native to the corn plant that underwent modification during the fermentation phase, as well as components added to the fermentation tank to promote the growth of the fermentation organism. It further comprises components that were a part of the fermentation organism, including cell materials, and products of cellular metabolism. The whole stillage is then transferred via line 14 to whole stillage storage tank 15 for further processing as described below to recover value-added by-products.

In another preferred embodiment soy material, preferably from the processing of soybeans, is utilized as additives to various stages of the ethanol and whole stillage production process and as a feedstock in various by-product recovery processes. This embodiment improves processing costs, as well as achieves value-added by-products. It is to be understood that alternative protein-containing materials, resulting from the processing of other protein-containing feedstock, such as whey, can also be utilized as additives to the various stages of the ethanol and whole stillage production and by-product recovery process.

In the preferred embodiment full fat soybeans are feed via line 16 to a conventional de-huller 17 to remove the soybean hulls. The removed soy hulls are then transferred via line 18 to a conventional mill 19 where they are ground to flour consistency; i.e., having a median particle size of less than about 100 microns. This soy hull flour is added to the fermentation tank 8 via line 20 where it is mixed with the extruded slurry to improve the rate of ethanol fermentation and to provide additional nutrients in the resultant whole stillage. In an alternate embodiment at least a portion of the soy hull flour is feed into extruder 3 via line 21 where it is mixed with the corn flour, water, enzymes, and additives, and then extruded.

The de-hulled and full fat soy meal recovered from de-huller 17 is then transferred via line 22 to mill 23 to achieve a soy flour; i.e., having a median particle size of less than about 100 microns. The soy flour is transferred via line 24 to mixer 25 where water from line 26 and additives from line 27 are mixed with the soy flour in mixer 26 to form a full fat soy slurry. The additives can include desired nutrients and enzymes. The selection of nutrients and enzymes is dependent on the desired value-added by-products desired to be recovered from the subsequent process steps.

In a preferred embodiment, a portion of this full fat soy slurry is transferred via line 28 to be combined with the whole stillage to increase the nutritional content of by-product "C" resulting from the extrusion and drying process described below. The remaining portion of the full fat solution is transferred via line 29 to microfiltration unit 30 to produce a defatted soy solution comprising proteins and other nutrients, and a retentate. The defatted soy solution can be recovered via line 31 as value-added by-product "A" that is useful in the formulation of neutraceuticals and in the paint industry for the production of acrylics.

The microfilter size should preferably be set so that the retentate includes soy oil, soy proteins, and soy carbohydrates, all combining to form an emulsion. A filter size of about 0.1 to 1.0 microns is preferred. The soy retentate emulsion is transferred via line 32 to dryer 33 to form value-added by-product "B". The drying conditions are preferably controlled to reduce the water content of by-product "B" to a level not conducive bacteria and fungi growth; i.e., less than about 12% water by weight. Such a by-product "B" can then be used in formulating various cosmetic and/or pharmaceutical products.

In a preferred embodiment a portion of the defatted soy solution from the microfiltration unit 30 is transferred via line 34 to a second extruder 35. In this embodiment of the invention additives via line 36 are mixed with the defatted soy solution in second extruder 35. The additives can include vitamins, minerals, amino acids, proteins, flavors, phytochemicals, pharmaceuticals, nutraceuticals, binders and fillers. It can also include other streams resulting from the treatment of carbohydrate-containing feedstock or processing of soybeans, or mixtures thereof.

In an alternate embodiment as described in more detail below and illustrated in FIG. 1 a nutrient-containing permeate stream from the treatment of the whole stillage can also be added via line 37 to the second extruder to thereby increase the nutritional content of the subsequently recovered by-products. In still another alternate embodiment the remaining portion of the defatted soy solution that is not feed to second extruder 35 can be transferred via line 38 to be mixed with the whole stillage for further processing as discussed below and illustrated in FIGS. 1 and 3.

It should be noted that use of microfiltration unit 30 to achieve a defatted soy solution is but one preferred method of producing the defatted soy solution. In an alternative preferred embodiment, the defatted soy solution can be produced directly by utilizing a commercially available soymeal that is already defatted and combining it with water and enzymes to form the desired soy solution.

In a preferred embodiment the extruded defatted soy solution is transferred via line 39 to first ultrafiltration unit 40 to form a nutrient-containing permeate stream and a soy protein retentate. The filter size of first ultrafiltration unit 40 is preferably sized and configured to have a molecular weight cut-off (MWCO) greater than about 1,000,000 to retain the soy protein from the extruded defatted soy solution. In a preferred embodiment the soy protein retentate is transferred via line 41 to dryer 42 where under time and temperature conditions a soy protein rich by-product "E" is formed and can be recovered via line 43. It is preferred that the operating conditions of dryer 42 be controlled to produce by-product "E" having less than about 12% water by weight. By-product "E" can then be used as a dietary nourishment value.

As illustrated in FIG. 2 the nutrient-containing permeate stream is preferably transferred via line 44 to a reverse osmosis filtration unit 45 designed to utilize high pressure (up to 5,000 psi or greater) and very small pore sizes to separate very low molecular weight materials, including vitamins, minerals, and soy carbohydrates, from the nutrient-containing permeate stream. These very low molecular weight materials are transferred via line 46 to dryer 47. It is preferred that the operating conditions of dryer 47 be controlled to produce by-product "I" having less than about 12% water by weight. The resulting by-product "I" can be recovered vial line 48 and used as a dietary supplement. The permeate (substantially water) from unit 45 can be re-circulated via line 49 to fermentation unit 8 or discharged into a water body, such as a lake, stream, or similar area.

In another preferred embodiment of the invention as illustrated in FIGS. 1 and 3, whole stillage from tank 15 is transferred via lines 50 and 51 to third extruder 52 or via lines 50 and 53 to second microfilter 54. Auxiliary nutrient containing materials or additives from line 55 are mixed with the whole stillage in extruder 52 to form an enhanced nutrient containing compound. The additives can be any ingredient in any amount that is needed to produce by-product "C" having the desired properties for its intended end use. Examples of such auxiliary nutrients include, but are not limited to, vitamins, minerals, amino acids, proteins, flavors, phytochemicals, pharmaceuticals, nutraceuticals, binders and fillers, other streams resulting from the treatment of carbohydrate-containing feedstock (such as the permeate from microfilter 54), streams resulting from the processing of soybeans (such as the full fat soy solution from mixer 25), as discussed below, and mixtures thereof.

The combined stillage and auxiliary materials are then extruded in the whole third extruder 52, under time, temperature, and pressure conditions to form an extruded compound. The extruded compound is transferred via line 56 to dryer 57 under time and temperature conditions to form a protein-rich nutrition by-product "C" having less than about 12% water by weight that can be recovered via line 58. By selection of the auxiliary materials by-product "C" will have an enhanced dietary nourishment value.

In another preferred embodiment, the remaining portion of the whole stillage not treated in the above discussed manner is transferred by line 53 to microfilter 54 to be further separated, based on molecular weight/particle size, into other value-added by-products. In this embodiment, microfilter 54 has a filter size of about 0.1 to 1.0 micron to produce a retentate stream, and a first nutrient-containing permeate stream. The permeate stream can be recycled via line 59 back to third extruder 52 to be thereby re-combined with the whole stillage and/or the other auxiliary materials indicated above. The filter size of the microfilter 54 should preferably be set to capture in the retentate stream various proteins and carbohydrates, fat globules, cell wall materials, and oils. These compounds all combine to form an emulsion that can be transferred by line 60 to dryer 61. It is preferred that the drying conditions be controlled to form by-product "D" having less than 12% water by weight. By-product "D" can be recovered by line 62 and used in the formulation of cosmetic and/or pharmaceutical products.

As indicated previously in another alternate preferred embodiment the first nutrient-containing permeate stream from the microfilter 54 can be transferred via line 37 to second extruder 35 where it is then combined with the defatted soy solution from microfilter 30 to thereby form a modified whole stillage stream that will increase the nutritional content of the subsequently recovered by-products "E" and "I", as discussed above, as well as by-products "F", "G" and "H" discussed below.

At this point, additional additives, such as vitamins, minerals, amino acids, proteins, flavors, phytochemicals, pharmaceuticals, nutraceuticals, binders, fillers, other streams resulting from the treatment of carbohydrate-containing feedstock, streams resulting from the processing of soybeans, and mixtures thereof, may also be introduced via line 63 to line 37 or via line 64 to line 39. Which additives and at what point in the process they are added is dependent on the particular by-products "E" through "I" that are desired.

Turning now to FIGS. 1 and 4 still another embodiment of the invention is illustrated. In this embodiment the permeate stream from line 37 is passed through additional filtering membranes for further separation into by-products "F" through "I". More particularly, the permeate from microfilter 54, with or without the permeate from second extruder 35, is transferred to ultrafiltration unit 65. As described above, additives from lines 63 or 64 can be introduced directly into the permeate stream 37 or stream 39 before it passes to ultrafiltration unit 65. If soybeans are not used in the process, then it is preferable that the additives from line 66 be added to line 67 feeding into ultrafiltration unit 65. The ultrafiltration units 65 and 68, nanofiltration unit 69 and reverse osmosis unit 45 will then be used to separate the protein materials of the additives from the non-protein components, and concentrate them along with the whole stillage proteins. After each stage of filtration, the resulting retentate streams are accumulated and transferred to dryers 70, 71, 72 and 47, respectively, via lines 73, 74, 75 and 46 whereby by-products "F", "G", "H" and "I", respectively, can be recovered from lines 76, 77, 78 and 48, respectively. Dryers 70, 71, 72 and 47, respectively, are operated under preferred time and temperature conditions, to create finished by-products with desirable functional characteristics. It is of course within the scope of this invention that one or more of the filtering units could be by-passed if a particular by-product is not desired.

In a preferred embodiment of the by-product recovery process, the nutrient-containing permeate stream from line 67 is then passed through ultrafiltration unit 65 to form another nutrient-containing permeate stream and another retentate stream. The filter size of ultrafiltration unit 65 is preferably sized and configured to have a molecular weight cut-off (MWCO) greater than 50,000 so as to retain the non-zein corn proteins in line 73 from the other nutrient-containing permeate in line 79. The non-zein protein retentate in line 73 is then dried under time and temperature conditions to form a non-zein protein rich product, referenced as by-product "F". The operating conditions in dryer 70 are controlled so that by-product "F" will have less than about 12% water by weight and will further have a flavor-enhancing value.

In another preferred embodiment the nutrient-containing permeate from ultrafiltration unit 65 will contain zein corn proteins. This permeate is then further passed via line 79 through ultrafiltration unit 68 to produce yet another nutrient-containing permeate stream and another retentate 61. Ultrafiltration unit 68 preferably comprises a filter membrane sized and configured to be of 10,000 MWCO to retain the zein corn proteins from the nutrient-containing permeate stream in line 79. The zein protein containing retentate in line 74 is subsequently dried under time and temperature conditions to produce a zein protein rich by-product "G". It is preferred that the operating conditions of dryer 71 be controlled to produce by-product "G" having less than about 12% water by weight and having a food coating value.

If specific carbohydrates are required, the nutrient-containing permeate in line 80 can be further passed through nanofiltration unit 69. The size of the filtering membrane is set to capture the particular carbohydrates desired. Examples would include various medium and low molecular weight dextrins that can be used as a water soluble glue, as thickening agents in food processing, or as binding agents in pharmaceuticals. They can also be used in pyrotechnics to add color to the explosion bursts. In a preferred embodiment the filtering membrane of nanofiltration unit 69 is sized and configured to be of 10,000 MWCO or less in order to retain low and medium molecular weight dextrins that is recovered in line 75. The dextrins can then be dried in dryer 72 to form a dextrin by-product "H" having less than about 12% water by weight. These dextrins that can be used as water soluble glues, as thickening agents in food processing, and as binding agents in pharmaceuticals. They can also be used in pyrotechnics to add color.

In another preferred embodiment a second enzyme (other than 1% alpha-amylase) is added to extruder 3 or elsewhere to promote the production of cyclodextrins during the fermentation step. This second enzyme is selected from those enzymes that are known to operate under the hydrolyzing and fermentation conditions and to do so in such a manner as not to interfere with the 1% alpha-amylase's production of ethanol. In this embodiment the filtering membrane of nanofiltration unit 69 is sized and configured to be of 2,000 MWCO in order to retain carbohydrates such as cyclodextrin that is recovered in line 75. The cyclodextrin retentate can then be dried in dryer 72 to form a cyclodextrin by-product "H" having less than about 12% water by weight that can be sold as a fiber source, and/or a carrier for organic chemicals, and/or a flavor source in the flavor industry. The cyclodextrins can also be used in analytical chemistry as a matrix for the separation of hydrophobic substances, as well as excipients in pharmaceutical formulations.

In another preferred embodiment additives such as those previously described can be added to one or more of the various permeate streams in lines 67, 79, 80 and 81 via lines 66, 82, 83 and 84, respectively, to further add nutrients or otherwise enhanced by-products "F", "G", "H" and "I", respectively. In another preferred embodiment each of the fully integrated soybean and corn feedstock processing steps set forth in FIG. 1 can be implemented so as to produce ethanol, as well as by-products "A" through "I".

While the invention has been described in terms of its preferred embodiments, other embodiments will be apparent to those of skill in the art from a review of the foregoing. Those embodiments as well as the preferred embodiments are intended to be encompassed by the scope and spirit of the following claims.

What is claimed is:

1. An improved ethanol production process comprising:
   (a) milling a carbohydrate-containing material to produce a carbohydrate-containing flour having a median particle size of less than about 100 microns;
   (b) hydrolyzing the carbohydrate-containing flour under operating conditions to form a mixture comprising partially gelatinized carbohydrate-containing flour and cleaved terminal amylose groups, wherein the terminal amylose groups are cleaved from the carbohydrate-containing flour;
   (c) dehulling full fat soybeans to produce soy hulls and de-hulled soy meal;
   (d) milling the soy hulls to produce a soy hull flour having a median particle size of less than about 100 microns;
   (e) adding the soy hull flour to the mixture to form a slurry, the slurry comprising the partially gelatinized carbohydrate-containing flour, the cleaved terminal amylose groups, and the soy hull flour;
   (f) fermenting the slurry to produce fermented slurry, the fermented slurry comprising ethanol and whole stillage; and
   (g) distilling the fermented slurry to separate the ethanol from the whole stillage.

2. The improved ethanol production process according to claim 1 further comprising:
   (a) milling the de-hulled soy meal to produce a de-hulled soy meal flour having a median particle size of less than about 100 microns;
   (b) mixing water with the de-hulled soy meal flour to form a de-hulled soy meal flour slurry;
   (c) filtering the de-hulled soy meal flour slurry through a microfilter having a pore size of about 0.1-1.0 microns to produce (i) a defatted soy solution comprising nutrients useful in the formulation of neutraceuticals or acrylic paint, and (ii) a retentate comprising soy oil, soy proteins and soy carbohydrates forming an emulsion;
   (d) filtering the whole stillage through a microfilter to form a whole stillage permeate; and
   (e) mixing said defatted soy solution with said whole stillage permeate.

3. The improved ethanol production process according to claim 2, further comprising drying the emulsion under conditions to reduce the water content of the emulsion to less than about 12% to form a product useful in formulating cosmetic or pharmaceutical products.

4. The improved ethanol production process according to claim 1, further comprising:
   (a) milling the de-hulled soy meal to produce a de-hulled soy meal flour having a median particle size of less than about 100 microns;
   (b) mixing water with the de-hulled soy meal flour to form a de-hulled soy meal flour slurry; and
   (c) mixing the de-hulled soy meal flour slurry with the whole stillage to form a stillage-slurry mixture.

5. The improved ethanol production process according to claim 4, further comprising:
   (a) mixing nutrients with the stillage-slurry mixture;
   (b) extruding the stillage-slurry mixture and nutrients mixed nutrients under extruding conditions comprising pressures of 300-3000 psi and temperatures of 100° C.-200° C. to form an extruded stream; and
   (c) drying the extruded stream to form a protein enriched product having a water content less than about 12% by weight.

6. The improved ethanol production process according to claim 1, further comprising:
   (a) mixing water and additives with the carbohydrate-containing flour in step (b) to form a slurry, wherein the additives comprise one or more enzymes in an amount of 0.5%-1.5% by dry weight.

7. The improved ethanol production process according to claim 6 wherein the additives include nutrients, and the ratio of the carbohydrate-containing flour, water, enzymes and nutrients in the slurry is about 100:20:1.5:1 to about 100:15:0.5:0.5 by weight.

8. The improved ethanol production process according to claim 7 wherein the mixing and hydrolyzing is performed in an extruder.

9. The improved ethanol production process according to claim 6 wherein the operating conditions during hydrolyzing comprises extruding at pressures of 300-3000 psi. temperatures of 100° C.-200° C., and for a time to cleave at 20%-40% of the terminal amylose groups from the carbohydrate-containing flour.

10. The improved ethanol production process according to claim 6 wherein:
(a) the carbohydrate-containing material is whole corn kernels;
(b) the operating conditions during hydrolyzing comprise pressures of about 500 psi and temperatures of 80° C.-130° C., for 45-60 seconds; and
(c) at least one of the enzymes functions to promote hydrolyzing the slurry and cleaving the terminal amylose groups.

11. The improved ethanol production process according to claim 1, further comprising filtering a dehulled soy flour of median particle size less than 100 microns, forming a permeate comprising a defatted soy solution and mixing the defatted soy solution with the whole stillage.

12. The improved ethanol production process according to claim 1, further comprising:
(a) after said distillation of said ethanol, filtering the whole stillage through a microfilter having a pore size of about 0.1-1.0 microns to produce (i) a nutrient-containing permeate and (ii) a retentate comprising proteins, carbohydrates, fat globules, cell wall materials and oil;
(b) drying the retentate to form a product having a water content of less than about 12% by weight useful in the formulation of cosmetic or pharmaceutical products.

13. The improved ethanol production process according to claim 12, further comprising:
(a) de-hulling full fat soybeans to produce soy hulls and de-hulled soy meal;
(b) milling the de-hulled soy meal to produce a de-hulled soy meal flour having a median particle size of less than about 100 microns;
(c) mixing water with the de-hulled soy meal flour to form a de-hulled soy meal flour slurry;
(d) filtering the de-hulled soy meal flour slurry through a microfilter having a pore size of about 0.1-1.0 microns to produce (i) a defatted soy solution and (ii) a retentate emulsion;
(e) mixing the defatted soy solution and the nutrient-containing permeate to form a modified whole stillage stream; and
(f) extruding the modified whole stillage stream to form a byproduct containing feedstock.

14. The improved ethanol production process according to claim 13, further comprising:
(a) filtering the byproduct feedstock through an ultrafilter configured to have a molecular weight cut-off greater than about 1,000,000 to produce (i) a soy protein containing retentate and (ii) a first permeate stream; and
(b) drying the soy protein containing retentate under conditions to produce a soy protein containing product having a water content less than about 12% by weight.

15. The improved ethanol production process according to claim 14, further comprising:
(a) filtering the first permeate stream through a reverse osmosis filtration unit capable of operating at pressures of at least 5000 psi. and having a pore size configured to separate vitamins, minerals and soy carbohydrates from the first permeate stream to form (i) a low molecular weight material containing retentate and (ii) a water-rich permeate; and
(b) drying the low molecular weight material retentate under conditions to produce a low molecular weight containing product having a water content less than about 12% by weight.

16. The improved ethanol production process according to claim 15, wherein said improved ethanol process is continuous and further comprises mixing at least a portion of the water-rich permeate with the carbohydrate-containing flour prior to hydrolyzing.

17. The improved ethanol production process according to claim 14, wherein the carbohydrate-containing material is corn, and further comprising:
(a) filtering the byproduct feedstock through a second ultrafilter laving a pore size configured to have a molecular weight cut-off greater than about 50,000 to produce (i) a non-zein protein containing retentate and (ii) a second permeate stream containing zein corn proteins; and
(b) drying the non-zein protein containing retentate under conditions to produce a non-zein protein containing product having a water content less than about 12% by weight.

18. The improved ethanol production process according to claim 17, further comprising:
(a) filtering the second permeate stream through a third ultrafilter having a pore size configured to have a molecular weight cut-off of about 10,000 to produce (i) a zein corn protein containing retentate and (ii) a third permeate stream containing medium and low molecular weight dextrins; and
(b) drying the zein corn protein containing retentate to produce a zein corn protein, containing product having a water content less than about 12% by weight.

19. The improved ethanol production process according to claim 18, further comprising:
(a) filtering the third permeate stream containing medium and low molecular weight dextrins through a nanofilter having a pore size configured to have a molecular weight cut-off less than about 10,000 to produce (i) a low and medium molecular weight dextrin containing retentate and (ii) a fourth permeate stream; and
(b) drying the low and medium molecular weight dextrin containing retentate to produce a dextrin containing product having a water content less than about 12% by weight.

20. The improved ethanol production process according to claim 18 further comprising:
(a) mixing water and additives with said carbohydrate containing flour prior to hydrolyzing, wherein the additives comprise one or more enzymes, wherein one of the enzymes is alpha-amylase and another of the enzymes is an enzyme other than alpha-amylase having an activity to promote the production of cyclodextrins during the fermenting;
(b) filtering the third permeate stream through a nanofilter having a pore size configured to have a molecular weight cut-off of 2,000 to produce (i) a cyclodextrin containing retentate and (ii) a fourth permeate stream; and
(c) drying the cyclodextrin containing retentate to produce a cyclodextrin containing product having a water content less than about 12% by weight.

* * * * *